United States Patent
Liu et al.

(10) Patent No.: US 12,042,486 B2
(45) Date of Patent: Jul. 23, 2024

(54) USE OF BULLEYACONITINE A

(71) Applicant: YUNNAN HAOPY PHARMACEUTICALS LTD, Yunnan (CN)

(72) Inventors: Xianguo Liu, Yunnan (CN); Biao Li, Yunnan (CN); Qiongfen Wu, Yunnan (CN)

(73) Assignee: YUNNAN HAOPY PHARMACEUTICALS LTD, Yunnan (CN)

( * ) Notice: Subject to any disclaimer, the term of this patent is extended or adjusted under 35 U.S.C. 154(b) by 693 days.

(21) Appl. No.: 17/293,941

(22) PCT Filed: Jun. 13, 2019

(86) PCT No.: PCT/CN2019/091049
§ 371 (c)(1),
(2) Date: May 14, 2021

(87) PCT Pub. No.: WO2020/103435
PCT Pub. Date: May 28, 2020

(65) Prior Publication Data
US 2022/0000846 A1 Jan. 6, 2022

(30) Foreign Application Priority Data
Nov. 19, 2018 (CN) .......................... 201811376531.5

(51) Int. Cl.
| | | |
|---|---|---|
| *A01N 37/00* | (2006.01) | |
| *A01N 25/00* | (2006.01) | |
| *A01N 37/12* | (2006.01) | |
| *A01N 37/44* | (2006.01) | |
| *A61K 9/00* | (2006.01) | |
| *A61K 9/08* | (2006.01) | |
| *A61K 9/20* | (2006.01) | |
| *A61K 9/28* | (2006.01) | |
| *A61K 9/48* | (2006.01) | |
| *A61K 9/70* | (2006.01) | |
| *A61K 31/215* | (2006.01) | |
| *A61K 31/24* | (2006.01) | |
| *A61K 31/439* | (2006.01) | |
| *A61K 47/02* | (2006.01) | |
| *A61K 47/44* | (2017.01) | |
| *A61P 17/04* | (2006.01) | |

(52) U.S. Cl.
CPC .......... *A61K 31/439* (2013.01); *A61K 9/0019* (2013.01); *A61K 9/08* (2013.01); *A61K 9/2013* (2013.01); *A61K 9/2059* (2013.01); *A61K 9/28* (2013.01); *A61K 9/4858* (2013.01); *A61K 9/4866* (2013.01); *A61K 9/4891* (2013.01); *A61K 9/7053* (2013.01); *A61K 47/02* (2013.01); *A61K 47/44* (2013.01); *A61P 17/04* (2018.01)

(58) Field of Classification Search
None
See application file for complete search history.

(56) References Cited

FOREIGN PATENT DOCUMENTS

| CN | 1087004 | A | * | 5/1994 |
|---|---|---|---|---|
| CN | 1257911 | C | * | 5/2006 |
| CN | 102552254 | A | | 7/2012 |
| CN | 105343070 | A | | 2/2016 |
| CN | 109453169 | A | | 3/2019 |

OTHER PUBLICATIONS

Ren et al. (Ethanolic extract of *Aconiti brachypodi* Radix attenuates nociceptive pain probably via inhibition of voltage-dependent Na$^+$ channel. Afr J Tradit Complement Altern Med. Jul. 1;9(4):574-83) (Year: 2012).*
European Patent Application No. 19888102.1; Extended Search Report; dated Apr. 5, 2022; 9 pages.
Yosipovitch et al.; "Itch: From mechanism to (novel) therapeutic approaches"; Journal of Allergy and Clinical Immunology; vol. 142; Nov. 2018; p. 1375-1390.
Huang et al.; "Bulleyaconitine A Inhibits and Itch Sensitization Induced by Histamine and Chloroquine"; Neuroscience; vol. 429; 2020; p. 68-77.
International Patent Application No. PCT/CN2019/091049; Int'l Written Opinion and Search Report; dated Aug. 15, 2019; 7 pages.
Li et al.; "Aconitum-Derived Bulleyaconitine A Exhibits Antihypersensitivity Through Direct Stimulating Dynorphin A Expression in Spinal Microglia"; The Journal of Pain; vol. 17; May 2016; p. 530-548.
Wang et al.; "Use of Bulleyaconitine A as an Adjuvant for Prolonged Cutaneous Analgesia in the Rat"; Anesth Analg.; vol. 107; Oct. 2008; p. 1397-1405.
Lee et al.; "A monoclonal antibody that targets a Nav1.7 channel voltage sensor for pain and itch relief"; Cell; vol. 157; Jun. 2014; p. 1393-1404.
Xie et al.; "Bulleyaconitine A attenuates hyperexcitability of dorsal root ganglion neurons induced by spared nerve injury: The role of preferably blocking Nav1.7 and Nav1.3 channels"; Molecular Pain; vol. 14; 2018; 13 pages.

* cited by examiner

*Primary Examiner* — Layla Soroush
(74) *Attorney, Agent, or Firm* — BakerHostetler

(57) ABSTRACT

The present disclosure belongs to the field of pharmaceuticals. Disclosed is a use of bulleyaconitine A in treating pruritus or a secondary lesion thereof, especially pruritus induced by histamine and/or chloroquine.

10 Claims, 2 Drawing Sheets

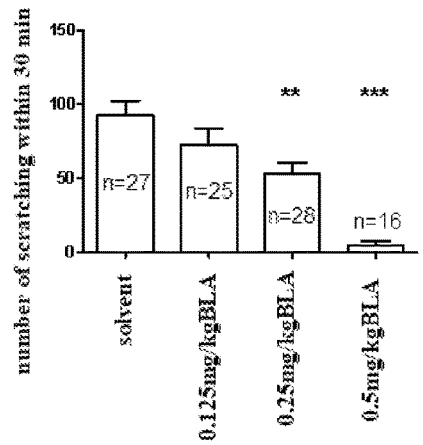

Fig. 3

When the dosage of a drug in per kg of body weight of animal A is known, and one wants to estimate the dosage of this drug in per kg of body weight of animal B, he may first check Table 3 on page 422 to find the conversion coefficient (W), and then calculate it by the following formula.

dosage in animal B (mg/kg) = W × dosage in animal A (mg/kg)

For example, it is known that the maximum tolerable dosage of a certain drug in mice is 20 mg/kg (0.4 mg for 20 g mice), one needs to convert it into the dosage in rabbits. It will be found that when animal A is a mice and animal B is a rabbit, the conversion coefficient at their crossover point is W = 0.37, so the dosage for rabbits is 0.37 × 20 mg/kg = 7.4 mg/kg, and the dosage for 1.5 kg rabbits is 11.1 mg.

Table 3  conversion coefficient of dosage in per kilogram of body weight between animal and human

| | conversion coefficient W | animal A or human | | | | | | |
|---|---|---|---|---|---|---|---|---|
| | | mouse | rat | guinea pig | rabbit | cat | dog | adult |
| | | 0.03kg | 0.2kg | 0.4kg | 1.5kg | 2kg | 12kg | 60kg |
| animal B or human | mouse 20g | 1.0 | 1.6 | 1.6 | 2.7 | 3.2 | 4.8 | 9.01 |
| | rat 0.2kg | 0.7 | 1.0 | 1.14 | 1.88 | 2.3 | 3.6 | 6.25 |
| | guinea pig 0.4kg | 0.61 | 0.87 | 1.0 | 1.65 | 2.05 | 3.0 | 5.55 |
| | rabbit 1.5kg | 0.37 | 0.52 | 0.6 | 1.0 | 1.23 | 1.76 | 2.30 |
| | cat 2.0kg | 0.30 | 0.42 | 0.48 | 0.81 | 1.0 | 1.44 | 2.70 |
| | dog 12kg | 0.21 | 0.28 | 0.34 | 0.56 | .068 | 1.0 | 1.88 |
| | adult 60kg | 0.11 | 0.16 | 0.18 | 0.304 | 0.371 | 0.531 | 1.0 |

Fig. 4

USE OF BULLEYACONITINE A

CROSS-REFERENCE TO RELATED APPLICATIONS

This application is a U.S. National Phase Application based upon PCT Application No. PCT/CN2019/091049, filed Jun. 13, 2019 which claims the priority to Chinese Patent Application No. 201811376531.5 titled "USE OF BULLEYACONITINE A", filed on Nov. 19, 2018 with the China National Intellectual Property Administration, which is incorporated herein by reference in entirety.

FIELD

The present disclosure relates to the technical field of medicine, and particularly relates to application of bulleyaconitine A.

BACKGROUND

Skin pruritus, also called as skin itching, is a common sensation related to the urge to scratch. Itchy skin may be caused by various factors, e.g., many clinical diseases, with very complicated etiology. Clinically, the one only present as itchy skin but without primary skin rashes is called as pruritus or skin pruritus. According to its location, skin pruritus can be classified into systemic skin pruritus and localized skin pruritus. The etiology of systemic dermatosis is mostly related to metabolic disorders and endocrine abnormalities. Some common causes are listed below. For senile skin pruritus, such itch is caused by the decline of sebaceous gland function, poor peripheral circulation, and the decline of water retention function of skin in the elderly, resulting that the skin becomes dry and susceptible to irritation caused by changes in the temperature of the surrounding environment. In addition, the lowered level of hormones in the elderly, e.g., sex hormones, which is more common in menopausal women, is also one of the causes of itch. For seasonal skin pruritus: such itch may occur due to the dry skin in winter or the irritation of heavily sweating in summer. Itch may also be caused by any skin pruritus resulting from systemic diseases, such as tumors, diabetes mellitus, kidney diseases, thyroid malfunction, anamia, and biliary diseases. Diabetes patients may be accompanied by systemic or localized skin itching, the occurrence of which is related to the accumulation of pyruvic acid and lactic acid in skin and nervous tissues during carbohydrate metabolism which then irritates nerve endings to itch. Hyperthyroidism is related to increased basal metabolism, hyperactivity, and hyperhidrosis in patients, while hypothyroidism is related to dry skin. Patients with kidney disease may undergo itch, because the accumulation of metabolic wastes, e.g., urea nitrogen and creatinine, as well as the excretion of part of urea from sweat glands, irritates skin to itch. And the itch will be more serious especially for the patients with uremia in the late stage of kidney disease.

Localized skin pruritus and systemic skin pruritus may be caused by same etiology, for example, tumors may cause systemic pruritus as well as localized pruritus in the patient. For this type of pruritus, the itch symptoms will disappear after the primary disease is under controlled. Some types of pruritus are also related to the patient's own spirit and emotions, such as, a typical example, the itching and discomfort appeared in the whole body or vulva of a patient with venereophobia. Systemic skin pruritus can present as systemic pruritus since the beginning of disease, or as localized at first and then spread to whole body. The degree of itch may be mild or severe. In mild cases, itch only happens at night, with no influence on daily work and life. But, in severe cases, one may suffer from unbearable itching both day and night painfully, so that they often scratch the skin unconsciously until bleeding, and even prick the skin with something sharp like knives, forks, scissors and nails until a feeling of severe pain. Due to long-term itching and troubles, such patients are often accompanied by some of nervousness, irritability, and being in bad temper for tiny things, which just aggravates the condition somewhat. In addition, because of long-term unconscious scratching, the skin becomes rough and mossy, and even with secondary lesions such as eczema, neurodermatitis, and prurigo nodularis. Itching often distresses patients, and seriously affects patient's sleep and rest, since it frequently occurs at night, which brings great pain and mental stress to patients and their families.

Currently, the common treatment for skin pruritus is oral administration of chlorphenamine, loratadine, cetirizine, mizolastine and other antihistamine, vitamin C, doxepin, oryzanol, diazepam, calcium gluconate, and so on. For patients with severe ill, they can take oral sedative-hypnotic drugs, or use corticosteroids preparation, procaine vein anesthesia, drugs for external use, e.g., calamine lotion, calamine menthol lotion, lotion or cream. But, these drugs show obvious drowsiness effects and serious side effects of hormonal drugs. Clinically, antihistamine H1 and H2 receptor antagonists, glucocorticoids, immunomodulation, as well as topical UV radiation therapy are mainly used in clinical treatments. However, they often cannot be applied for a long time due to adverse reactions, and once the treatment is interrupted, the pruritus recurs quickly. Therefore, it is required to develop safe, effective and affordable drugs for skin pruritus.

Bulleyaconitine A (BLA) is an alkaloid isolated from an *Aconitum* plant *Aconitum* Bulleyanum Diels, a medicinal plant grows only in Dianxi. BLA has good anti-inflammatory, analgesia and immunomodulation effects. Bulleyaconitine A, being a new type-III analgesic drug, but not a NSAID, is able to regulate sodium ion channels and almost products no psychological dependence and toxic effects on organic organs, thereby avoiding the adverse reactions on gastrointestinal tract and cardiovascular as well as kidney, drug dependence, and other potential risks caused by NSAID and opioid analgesics. Currently, it has been widely applied clinically to treat rheumatoid arthritis (RA), osteoarthritis, myofibrositis, neck and shoulder pain, waist and leg pain, cancer pain and chronic pain caused by various reasons. However, there has no reports so far on the action and efficacy of bulleyaconitine A for treating skin pruritus. In addition, bulleyaconitine A, being a medicinal monomer, is an active drug extracted from Chinese herbal medicine, and possess several characteristics, e.g., good safety, fewer side effects, and no addiction. Therefore, it has a promising prospect in market to further study bulleyaconitine A isolated from a Chinese herbal extract.

SUMMARY

In view of that, the present disclosure provides use of bulleyaconitine A. Medicament prepared from bulleyaconitine A for treating skin pruritus has reliable curative effect and has no toxic side effects on liver and kidney, thus it can be taken for a long period, to suppress the recurring skin pruritus and avoid roughness and lichenification of skin as well as secondary lesions, e.g., eczema, neurodermatitis, prurigo nodularis, as a result of unconsciously scratching.

In order to achieve the above objectives of this invention, the present disclosure provides the following technical solutions.

The present disclosure provides use of bulleyaconitine A in preparation of a medicament for treating and/or preventing skin pruritus and/or a secondary lesion thereof.

In some particular embodiments of the present disclosure, a dosage of bulleyaconitine A is 0.125 mg/kg mouse body weight/d–0.5 mg/kg mouse body weight/d.

In some particular embodiments of the present disclosure, a dosage of the bulleyaconitine A is 0.01375 mg/kg human body weight/d–0.055 mg/kg human body weight/d.

In some particular embodiments of the present disclosure, the skin pruritus is neuropathic itch.

In some particular embodiments of the present disclosure, the skin pruritus is caused by histamine and/or chloroquine.

In some particular embodiments of the present disclosure, the medicament comprises bulleyaconitine A, which is present in an amount of 0.2%-88% by mass of the medicament, and a pharmaceutically acceptable carrier.

In some particular embodiments of the present disclosure, the medicament is in a dosage form of oral preparation, injection preparation or external preparation.

In some particular embodiments of the present disclosure, the oral preparation includes hard capsules, dripping pills, granules, tablets, mixtures, soft capsules, concentrated pills, oral liquid solutions or powders.

In some particular embodiments of the present disclosure, the injection preparation is injection solution or lyophilized powder for injection.

In some particular embodiments of the present disclosure, the external preparation includes tincture, ointment, cream, paste, aerosol, spray, powder, otic preparation, lotion, rinse, liniment, paint, film preparation, gelatin or patch.

The present disclosure provides new application of bulleyaconitine A, whose mechanism is possibly that by regulating sodium ion channels, it inhibits the specific neurons specifically responsible for transmission of itch in the peripheral and central nervous system, or maybe that by regulating sodium ion channels, it inhibits the activation and transmission of itch mediators as well as the regulation of selective receptors for itching substances, thereby inhibiting itching.

1. The application of bulleyaconitine A in treatment of skin pruritus can avoid the unavailable long-term use of drugs likes antihistamines and hormones due to adverse reactions and avoid the recurrence of itching.

2. The application of bulleyaconitine A in treatment of skin pruritus has reliable curative effect and no toxic side effects on liver and kidney, thus it can be taken for a long period, to suppress the recurring skin pruritus and avoid roughness and lichenification of skin as well as secondary lesions, e.g., eczema, neurodermatitis, prurigo nodularis, as a result of unconsciously scratching.

3. The application of bulleyaconitine A in treatment of skin pruritus can relieve the patient's distress for itching, as well as effectively relieve their and their family's pain and mental stress due to frequently occurred itch at night and serious effect on their sleep and rest.

BRIEF DESCRIPTION OF DRAWINGS

In order to more clearly illustrate the technical solutions in the examples of the present disclosure or the prior art, hereinafter, a brief introduction will be made to the drawings that need to be used in the description of the examples or the prior art.

FIG. 3 shows the number of scratching in the chloroquine group within 30 min (: $P<0.01$ as compared to the solvent group; *: $P<0.001$ as compared to the solvent group); and FIG. 4 shows the conversion relationship between animal dosages, and for more details, one may see Table 3 on page 422 of "Experimental Zoology for Medicine" by Xinyou Shi.

DETAILED DESCRIPTION

The application of bulleyaconitine A is disclosed in the present disclosure, but it is possible for those skilled in the art to learn from the content disclosed herein and appropriately improve the process parameters to realize it. It should be particularly noted that all similar substitutions and modifications that are obvious to those skilled in the art are considered to be included in the present disclosure. The methods and applications of the present disclosure have been described through preferred embodiments, it is obvious that those skilled in the art can modify or appropriately change and combine these methods and applications described herein to realize and implement the technique of the present disclosure, without departing from the content, spirit and scope of the present disclosure.

Term Explanation:

Skin pruritus refers to a group of dermatosis characterized by itchy skin, including the pruritus only present as the itchy skin but lack of the primary skin rashes, and the conditions coexisting the itchy skin and the primary skin rashes, e.g., neurodermatitis, prurigo, prurigo nodularis.

Skin pruritus or secondary lesions thereof: "secondary lesions" refers to skin roughness, lichenification, eczema, neurodermatitis, prurigo nodularis and other disorders, as a result of recurring skin pruritus and scratching.

The raw materials and reagents used in the application of bulleyaconitine A provided by the present disclosure are all commercially available.

The present disclosure will be further described below in conjunction with examples.

Example 1

The Purpose of the Experiment:

Researches over the years have shown that itch is mainly transmitted by two types of C fibers, with one sensitive to histamine and the other to chloroquine. Therefore, the scratching response of animals caused by subcutaneous injection of histamine or chloroquine is internationally recognized as an acute itch model. The present disclosure is aimed to investigate whether the intragastric administration of bulleyaconitine A (BLA) can inhibit acute itch caused by histamine or chloroquine.

Figure 1:
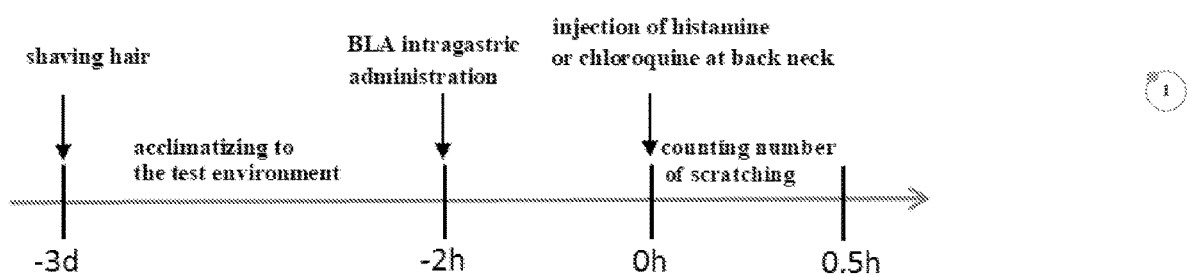
FIG. 1 shows the experimental process, wherein BLA is bulleyaconitine A, D is day, and h is hour.

Experimental Materials and Methods:

6-8 weeks old C57 mice were employed in experiments (body weight of 17-20 grams, from the Experimental Animal Center of Sun Yat-Sen University). The mice were randomly divided into four groups, namely solvent+histamine control group, BLA+histamine group, solvent+chloroquine control group and BLA+chloroquine group. For the convenience of subcutaneous injection and observation of scratching, the hair around the neck and back (at least 3×5 cm) was shaved off under temporary anesthesia with isoflurane three days before the start of the experiments. The control group was given a subcutaneous injection of 50 μl of histamine (2 mg/ml) or chloroquine (4 mg/ml), with an intragastric administration of a solvent (carboxymethyl cellulose) 2 hours before the injection. The experiment group was given an intragastric administration of BLA with different dosages (0.125, 0.25 and 0.5 mg/kg), 2 hours before the injection of histamine or chloroquine. The BLA was administered 2 hours in advance, because it needs 1.5-2 hours for BLA to take effect from its intragastric administration. The number of scratching in each group was counted within 30 minutes for comparison, because the acute scratching response induced by histamine or chloroquine subsided 30 minutes later after drug injection as shown by previous studies. The experimental process is shown in FIG. 1.

During the recording in experiment, the mice were placed in separate, transparent acrylic boxes having a size of 15×15×20 cm each, and with two small openings at top of each box to allow air to circulate. The scratching behavior was recorded as video by a camera, which was placed above mouse because their behaviors of scratching their back or neck mostly happen in an angle of view directly opposite to their upper back.

The scratching behavior can be easily suppressed by attention distraction. In order to minimize attentional shift and eliminate tension as much as possible, each transparent box was supplied with a small amount of padding, to absorb any urine excreted from the mouse. The ambient temperature was kept at 23-27° C., and additionally all the staff were asked to leave during the recording to keep the experimental environment quiet. The experiment was carried out between 9:00-14:00 h. To acclimatize the animals to the test environment, the mouse had been acclimatized in the transparent box for one hour at 9:00 and 13:00 every day since two days before the formal experiment. Because the scratching of a mice often happens quickly, the action from mice starting to scratch its neck or back by its hind paw until the hind paw hitting on the ground or being put into its mouth to clean the dander is taken as one scratching behavior.

Statistical methods: the number of scratching was represented by average value±standard deviation, and Turkey test was employed to compare the difference between different groups.

Solution preparation and application method: 0.05 g of BLA was weighed and dissolved in 1000 ml of 0.5% sodium carboxymethyl cellulose solution. Histamine and chloroquine were prepared with 0.9% sterile saline, to make a dosage of histamine 100 μg and chloroquine 200 μg. To minimize the skin injure at the injection site, a thinner needle in 0.3 ml for insulin was connected to the needle port of the microinjector to reduce injure to mouse.

Figure 2:
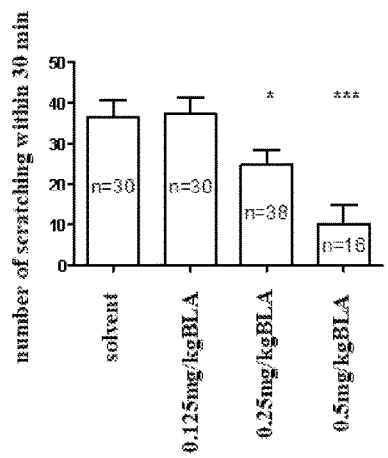
FIG. 2 shows the number of scratching in the histamine group within 30 min (*: $P<0.05$ as compared to the solvent group; ***: $P<0.001$ as compared to the solvent group)

Experimental Results:

As shown in the experimental results in Table 1, the number of scratching in mouse within 30 minutes before subcutaneous injection of histamine or chloroquine was 3.42±2.40, while the number of scratching within 30 minutes after injection of histamine or chloroquine was respectively increased to 29.42±16.63 (n=12) or 73.75±34.11 (n=12), indicating that the model was made successfully. BLA inhibited the itch caused by histamine or chloroquine in a manner of depending on the dosage of intragastric administration. As shown in Table 2-3 and FIGS. 2-3, at the dosage of 0.5 mg/kg, BLA completely inhibited ($P<0.001$) the acute itch caused by histamine or chloroquine, showing the strongest inhibitory effect, but drowsiness in mouse was observed; at the dosage of 0.25 mg/kg, BLA significantly inhibited the scratching response caused by histamine ($P<0.05$) or chloroquine ($P<0.01$); but at the dosage of 0.125 mg/kg, BLA did not inhibit the itching caused by histamine, showing no inhibitory effect, and only had slightly inhibitory effect on the acute itch caused by chloroquine, which did not reach a statistically significant level ($P>0.05$). At the latter two dosage, no drowsiness or other side effects in mouse was observed.

TABLE 1

Comparison of the number of itching before and after injection

| | Group | | |
|---|---|---|---|
| No. | con | histamine | chloroquine |
| 1 | 2 | 0 | 33 |
| 2 | 6 | 21 | 108 |
| 3 | 7 | 33 | 52 |
| 4 | 4 | 53 | 90 |
| 5 | 1 | 60 | 98 |
| 6 | 4 | 33 | 44 |
| 7 | 0 | 20 | 94 |
| 8 | 5 | 26 | 52 |
| 9 | 2 | 4 | 16 |
| 10 | 0 | 38 | 80 |
| 11 | 7 | 36 | 142 |
| 12 | 3 | 29 | 76 |
| Average number | 3.4216666667 | 29.421666667 | 73.75 |
| Standard deviation | 2.40396467307 | 16.632557434 | 34.11286414 |

TABLE 2

Number of scratching in mouse in the histamine group between 2 hours and 2.5 hours after intragastric administration of BLA

| | Group | | | |
|---|---|---|---|---|
| No. | solvent + histamine | 0.125 mg/kg BLA + histamine | 0.25 mg/kg BLA + histamine | 0.5 mg/kg BLA + histamine |
| 1 | 0 | 25 | 0 | 0 |
| 2 | 21 | 22 | 12 | 0 |
| 3 | 33 | 33 | 0 | 0 |
| 4 | 53 | 0 | 4 | 0 |
| 5 | 60 | 18 | 1 | 0 |
| 6 | 33 | 47 | 3 | 0 |
| 7 | 20 | 43 | 4 | 0 |
| 8 | 26 | 77 | 0 | 0 |
| 9 | 4 | 60 | 43 | 0 |
| 10 | 38 | 46 | 5 | 0 |
| 11 | 36 | 42 | 0 | 0 |
| 12 | 29 | 16 | 7 | 0 |
| 13 | 41 | 21 | 0 | 50 |
| 14 | 72 | 87 | 0 | 38 |
| 15 | 37 | 26 | 26 | 48 |
| 16 | 30 | 17 | 23 | 26 |
| 17 | 6 | 38 | 12 | |
| 18 | 34 | 37 | 23 | |
| 19 | 33 | 3 | 50 | |
| 20 | 50 | 84 | 64 | |
| 21 | 51 | 35 | 13 | |
| 22 | 50 | 43 | 14 | |
| 23 | 31 | 38 | 25 | |
| 24 | 20 | 18 | 63 | |
| 25 | 33 | 38 | 9 | |
| 26 | 55 | 64 | 53 | |
| 27 | 91 | 46 | 18 | |
| 28 | 21 | 52 | 56 | |
| 29 | 89 | 43 | 35 | |

TABLE 2-continued

Number of scratching in mouse in the histamine group between 2 hours and 2.5 hours after intragastric administration of BLA

| No. | solvent + histamine | 0.125 mg/kg BLA + histamine | 0.25 mg/kg BLA + histamine | 0.5 mg/kg BLA + histamine |
|---|---|---|---|---|
| 30 | 0 | 6 | 38 | |
| 31 | | | 33 | |
| 32 | | | 7 | |
| 33 | | | 32 | |
| 34 | | | 70 | |
| 35 | | | 41 | |
| 36 | | | 48 | |
| 37 | | | 43 | |
| 38 | | | 66 | |
| average number | 36.56667 | 37.5 | 24.76315789 | 10.1325 |
| standard deviation | 22.15203 | 21.60054012 | 22.07097905 | 18.17235194 |

The concentrations tested in mouse are roughly equivalent to 0.11×0.125 mg/kg=0.01375 mg/kg, 0.11×0.25 mg/kg=0.0275 mg/kg, and 0.11×0.5 mg/kg=0.055 mg/kg in adults, that is, bulleyaconitine A has a certain effect of inhibiting acute itch in the test with concentrations equivalent to those of the adults ranging from 0.01375 mg/kg to 0.055 mg/kg.

Example 2

The application of bulleyaconitine A in neuropathic itch of the present disclosure can be implemented by preparing bulleyaconitine A into a medicament in different dosage forms. In particular, bulleyaconitine A can be prepared into dosage forms including oral preparations, injection preparations or external preparations. Specific medicament can contain bulleyaconitine A and other pharmaceutically acceptable carriers. The amount of each component in the medicament can be adjusted according to the requirements for the component ratio in pharmaceutical preparations. The effective amount of bulleyaconitine A can also be calculated

TABLE 3

Number of scratching in mouse in the chloroquine group between 2 hours and 2.5 hours after intragastric administration of BLA

| No. | solvent + chloroquine | 0.125 mg/kg BLA + chloroquine | 0.25 mg/kg BLA + chloroquine | 0.5 mg/kg BLA + chloroquine |
|---|---|---|---|---|
| 1 | 33 | 93 | 75 | 0 |
| 2 | 108 | 45 | 0 | 0 |
| 3 | 52 | 29 | 43 | 0 |
| 4 | 90 | 70 | 75 | 0 |
| 5 | 98 | 90 | 136 | 0 |
| 6 | 44 | 31 | 0 | 0 |
| 7 | 94 | 115 | 33 | 0 |
| 8 | 52 | 185 | 101 | 0 |
| 9 | 16 | 89 | 25 | 0 |
| 10 | 80 | 40 | 0 | 0 |
| 11 | 142 | 130 | 38 | 0 |
| 12 | 76 | 23 | 26 | 0 |
| 13 | 156 | 197 | 30 | 27 |
| 14 | 87 | 24 | 78 | 0 |
| 15 | 238 | 24 | 34 | 20 |
| 16 | 101 | 53 | 78 | 23 |
| 17 | 193 | 10 | 37 | |
| 18 | 83 | 182 | 10 | |
| 19 | 53 | 27 | 64 | |
| 20 | 68 | 26 | 78 | |
| 21 | 40 | 138 | 118 | |
| 22 | 145 | 48 | 53 | |
| 23 | 77 | 41 | 17 | |
| 24 | 78 | 62 | 25 | |
| 25 | 84 | 34 | 23 | |
| 26 | 108 | | 143 | |
| 27 | 103 | | 80 | |
| 28 | | | 47 | |
| average number | 92.565556 | 72.24 | 52.39285714 | 4.3875 |
| standard deviation | 48.010643 | 54.713327444 | 38.67293192 | 9.191538228 |

The above test results showed that oral administration of bulleyaconitine A can inhibit the itching caused by histamine or chloroquine in a dosage-dependent manner. Therefore, oral administration of bulleyaconitine A can be used to treat neuropathic itch caused by various diseases and drugs.

according to the conventional requirements of various dosage forms, for example, a range from 0.01375 mg/kg to 0.055 mg/kg human body weight/d as described in Example 1 is only given as a reference range to this example, while it is not a specific limitation. Furthermore, the pharmaceutically acceptable carriers can include, but not limit to, flavoring agents including glucose, sorbitol, and mannitol; fillers including microcrystalline cellulose; disintegrating agents including potassium hydroxymethyl starch; coloring agents and thickeners.

Example 3

A table containing bulleyaconitine A, which was a film-coated tablet, containing 0.275 mg of bulleyaconitine A and 130 mg of adjuvants in each tablet was prepared as follows. Bulleyaconitine A was dissolved in food grade or pharmaceutical grade ethanol. 20 mg of adjuvant lactose, 25 mg of icing sugar, 40 mg of microcrystalline cellulose and 10 mg of hydroxypropyl cellulose were mixed, and then added with the ethanol solution of bulleyaconitine A to mix. The resultant was prepared into a soft material with an appropriate amount of purified water added, and then into granules. After the granules was dried, 5 mg of magnesium stearate and 30 mg of sodium carboxymethyl starch were added, and tableted, and then film-coated.

Example 4

A capsule of bulleyaconitine A, containing 0.4 mg of bulleyaconitine A and 165 mg of adjuvants in each capsule, was prepared as follows. Bulleyaconitine A and adjuvants, namely 80 mg of icing sugar, 25 mg of starch, 20 mg of microcrystalline cellulose, 15 mg of low-substituted hydroxypropyl cellulose, 5 mg of magnesium stearate and 5 mg of phthalate were prepared into a soft material with ethanol added as a wetting agent, and then into pellets, dried, coated with 15 mg of polyacrylic resin as enteric coating. The dried pellets were cooled to room temperature, and then coated with polyacrylic resin. After the coated pellets were filled into hard capsules, internally and externally packaged to obtain the finished pellet capsules.

Example 5

A controlled release tablet of bulleyaconitine A, containing 0.98 mg of bulleyaconitine A in each table was prepared as follows. Bulleyaconitine A, matrix materials (hypromellose 125 mg), and lubricant (magnesium stearate 1 mg) were mixed well, and pressed into tables by a tablet compressing machine. The obtained tables were coated with coating materials by a film coating machine.

Example 6

An injection solution of bulleyaconitine A, containing 2 mg of bulleyaconitine A per ml was prepared as follows. 2000 mg of bulleyaconitine A was weighed, dissolved by adding 5 ml of dilute sulfuric acid, and added with water for injection to a volume of 1000 ml, with pH adjusted to 5.0, filtered, filled, encapsulated, and sterilized.

Example 7

A bulleyaconitine A for injection, containing 0.2 mg of bulleyaconitine A in each bottle was prepared as follows. 200 mg of bulleyaconitine A was weighed and dissolved by adding 5 ml of dilute sulfuric acid, added with water for injection to a volume of 500 ml, and added with 200 g of mannitol to dissolve, and then added with water for injection to a volume of 1000 ml, with pH adjusted to 5.0, filtered, filled and encapsulated to 1000 bottles, stoppered, freeze-dried and compacted by press.

Example 8

A patch of bulleyaconitine A, containing 4 mg of bulleyaconitine A in each patch was prepared as follows. 4000 mg of bulleyaconitine A, 150000 mg of silicone pressure sensitive adhesive, 2000 mg of eucalyptus oil were weighed, after bulleyaconitine A was dissolved by adding 100 ml of ethanol, it was mixed well with the silicone pressure sensitive adhesive and eucalyptus oil. The mixture was coated on a polytetrafluoroethylene film protective layer, with the thickness of the coating controlled, to make 1000 patches, dried, covered with a non-woven backing layer, and then cut into an appropriate shape and size.

Example 9

A tablet containing bulleyaconitine A, containing 3.3 mg of bulleyaconitine A in each table, was prepared as follows. 3300 mg of bulleyaconitine A, 3000 mg of lactose, 1500 mg of hydroxypropyl cellulose, 50 mg of magnesium stearate, and 400 mg of sodium carboxymethyl starch were mixed well, and pressed into 1000 tablets using direct press.

Example 10

A tablet containing bulleyaconitine A, containing 3.3 mg of bulleyaconitine in each table was prepared as follows. 3300 mg of bulleyaconitine A, 250 mg of lactose, 100 mg of hydroxypropyl cellulose, 50 mg of magnesium stearate, and 50 mg of sodium carboxymethyl starch were mixed well, and pressed into 1000 tablets using direct press.

The application of bulleyaconitine A provided by the present disclosure is introduced in detail above. To illustrate the principle and implementation of the present disclosure, specific examples are used herein, but their description above is only given to facilitate understanding of the method and core concept of the present disclosure. It should be noted that for those skilled in the art, various improvements and modifications can be made without departing from the principle of the present disclosure, and these improvements and modifications should fall within the scope of protection of the present disclosure.

The invention claimed is:

1. A method of treating skin pruritus and/or a secondary lesion thereof, comprising administering bulleyaconitine A to a subject in need thereof, wherein the secondary lesion is selected from eczema, neurodermatitis, and prurigo nodularis.

2. The method according to claim 1, wherein the subject is a mouse, and wherein a dosage of bulleyaconitine A is 0.125 mg/kg mouse body weight per dose—0.5 mg/kg mouse body weight per dose.

3. The method according to claim 1, wherein the subject is a human, and wherein a dosage of the bulleyaconitine A is 0.01375 mg/kg human body weight per dose—0.055 mg/kg human body weight per dose.

4. The method according to claim 1, wherein the skin pruritus is neuropathic itch.

5. The method according to claim 4, wherein the skin pruritus is an itch caused by at least one of a histamine and a chloroquine.

6. The method according to claim 1, wherein bulleyaconitine A is present in a medicament which comprises a pharmaceutically acceptable carrier, and bulleyaconitine A is present in the medicament in an amount of 0.2%-88% by mass of the medicament.

7. The method according to claim 6, wherein the medicament is in a dosage form of oral preparation, injection preparation or external preparation.

8. The method according to claim 7, wherein the oral preparation includes at least one of: hard capsules, dripping pills, granules, tablets, mixtures, soft capsules, concentrated pills, oral solutions and powders.

9. The method according to claim 7, wherein the injection preparation is injection solution or lyophilized powder for injection.

10. The method according to claim 7, wherein the external preparation is tincture, ointment, cream, paste, aerosol, spray, powder, otic preparation, lotion, rinse, liniment, film, or patch.

* * * * *